US00PP28279P3

(12) United States Plant Patent
Lee

(10) Patent No.: US PP28,279 P3
(45) Date of Patent: Aug. 15, 2017

(54) ***RHODODENDRON* PLANT NAMED 'ROBLEZ'**

(50) Latin Name: ***Rhododendron* hybrid**
Varietal Denomination: ROBLEZ

(71) Applicant: Robert Edward Lee, Independence, LA (US)

(72) Inventor: Robert Edward Lee, Independence, LA (US)

(73) Assignee: Plant Development Services, Inc, Loxley, AL (US)

( * ) Notice: Subject to any disclaimer, the term of this patent is extended or adjusted under 35 U.S.C. 154(b) by 144 days.

(21) Appl. No.: 14/545,615

(22) Filed: May 29, 2015

(65) Prior Publication Data

US 2016/0353626 P1 Dec. 1, 2016

(51) Int. Cl.
*A01H 5/00* (2006.01)

(52) U.S. Cl.
USPC ..... Plt./240

(58) Field of Classification Search
USPC ..... Plt./226, 238, 240
See application file for complete search history.

(56) References Cited

PUBLICATIONS

PLUTO: Plant Variety Database, Dec. 8, 2016, citation for 'Roblez'. 1 page.*
Schepker et al. 2010. Autumn-blooming *Rhododendron* varieties. *Rhododendron* and Immergruence; vol. 9: 31-36. 3 pages.*
Schepker et al. 2010—partial English translation. 4 pages.*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Rhododendron* cultivar named 'ROBLEZ' is disclosed, characterized by distinctive semi-double red flowers. Plants bloom Spring, Summer and Fall and exhibit good tolerance for both hot and cold conditions. The new cultivar is a *Rhododendron*, suitable for ornamental garden purposes.

1 Drawing Sheet

Latin name of the genus and species: *Rhododendron* hybrid.

Variety denomination: 'ROBLEZ'.

BACKGROUND OF THE INVENTION

The new cultivar is a product of a planned breeding program by the inventor, Robert Edward Lee. The inventor's intention was to develop *Rhododendron* hybrid plants with re-blooming characteristics. This new variety, hereinafter referred to as 'ROBLEZ', was discovered as a seedling, resulting from the crossing of *Rhododendron* 'Red Slipper', unpatented with the pollen parent *Rhododendron* 'Arabesk', unpatented. The cross resulting in the new variety occurred during 2004. The new variety was selected by the inventor during November of 2007 at a commercial nursery in Independence, La.

After identifying the new variety as a potentially interesting selection, the inventor first organized propagation of 'ROBLEZ' by vegetative cuttings Fall of 2007 at the same commercial nursery in Independence, La. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEZ' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEZ' These characteristics in combination distinguish 'ROBLEZ' as a new and distinct *Rhododendron* cultivar:

1. Unique Spring, Summer, and Fall blooming.
2. Clear red flowers.
3. Compact plant habit.
4. Tolerant of both warm and cold environmental conditions.
5. Distinctive semi-double flower.
6. Very good foundation plant.
7. Hardy to Zone 6.
8. Uniform, globular plant shape.

COMPARISON TO PARENT VARIETY

'ROBLEZ' is similar in most horticultural characteristics to the seed parent *Rhododendron* hybrid 'Red Slipper'. Plants of the new cultivar 'ROBLEZ' however differ in the following:

1. The new variety has a darker red flower
2. The new variety blooms more consistently over three seasons.
3. Plants of the new variety are more compact.
4. Foliage of the new variety is darker green.
5. Plants of the new variety are more tolerant of both hot and cold conditions.

'ROBLEZ' is similar in most horticultural characteristics to the pollen parent *Rhododendron* hybrid 'Arabesk'. Plants of the new cultivar 'ROBLEZ' however differ in the following:

1. 'ROBLEZ' produces semi-double flower, flowers of 'Arabesk' are single.
2. The new variety has a darker red flower
3. The new variety blooms more consistently over three seasons.
4. Plants of the new variety are more compact.
5. Foliage of the new variety is darker green.
6. Plants of the new variety are more tolerant of both hot and cold conditions.

COMMERCIAL COMPARISON

'ROBLEZ' can be compared to the commercial variety *Rhododendron* hybrid 'Conlef' U.S. Plant Pat. No. 10,579. Plants of the new cultivar 'ROBLEZ' are similar to plants of 'Conlef' in most horticultural characteristics, however, plants of the new cultivar 'ROBLEZ' differ in the following:

1. 'Roblez' has semi-double red flowers, 'Conlef' has single red/pink flowers.
2. Plants of 'Roblez' are more compact than plants of 'Conlef'.

'ROBLEZ' can be compared to the commercial variety *Rhododendron* hybrid 'Conleb' U.S. Plant Pat. No. 10,581. Plants of the new cultivar 'ROBLEZ' are similar to plants of 'Conleb' in most horticultural characteristics, however, plants of the new cultivar 'ROBLEZ' differ in the following;

1. 'Roblez' has dark red flowers, 'Conleb' has orange-red flowers
2. Plants of 'Roblez' are more compact.
3. Foliage of 'Roblez' is smaller and darker.
4. Plants of the new variety are more tolerant cold conditions.

BRIEF DESCRIPTION OF THE PHOTOGRAPH

The accompanying photograph in the FIGURE illustrates in full color a close up of typical flowers of the new variety. Age of the plant is approximately 2 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ROBLEZ' plants grown outdoors in Loxley, Ala. Plants are approximately 2 years old, in a 3 gallon nursery container. Measurements and numerical values represent averages of typical plant types.

Botanical classification: *Rhododendron* hybrid 'ROBLEZ'.

Propagation: Typically by semi-hardwood cuttings in Spring and Summer.

Root description: Fine, fibrous young roots, well branched. Colored near RHS Grey-Brown 199A.

PLANT

Growth habit: Compact, globular shrub.

Height: Approximately 32 cm to top of foliar and flowering plane.

Plant spread: Approximately 50 cm.

Branching characteristics: Well branched, approximately 4 primary branches from the center of the plant. Branches occur at approximately 45° to 75° angles. Each primary branch has 4 to 8 lateral branches.

Primary branches:

- *Length of primary branches.*—Average 15 cm.
- *Diameter of primary branches.*—Approximately 0.6 cm.
- *Primary branch strength.*—Very strong, difficult to break.
- *Primary branch color.*—Young primary branches near RHS Yellow-Green N144D; oldest branches become woody, colored near Brown 200B.
- *Primary branch texture.*—Immature growth hirsute. Older growth scaly, hirsute.

Lateral branches:

- *Number of lateral branches.*—Approximately 4 to 8 per primary branch.
- *Length of lateral branches.*—Average 7 cm.
- *Diameter of lateral branches.*—Average 0.4 cm.
- *Lateral branch strength.*—Very strong, flexible.
- *Lateral branch color.*—Immature branches near RHS Greyed-Purple 183A, turning, Yellow-Green N144D.
- *Lateral branch texture.*—Hirsute.
- *Internode length.*—Average 1.0 cm.

Age of plant described: Approximately 2 years.

FOLIAGE

Leaf:

- *Type.*—Simple.
- *Arrangement.*—Alternate.
- *Average length.*—Approximately 4.4 cm.
- *Average width.*—Approximately 2.2 cm.
- *Shape of blade.*—Obovate to nearly spatulate.
- *Apex.*—Mucronate.
- *Base.*—Broad attenuate.
- *Attachment.*—Stalked.
- *Margin.*—Entire.
- *Texture of top surface.*—Pubescent. Hairs appressed.
- *Texture of bottom surface.*—Pubescent. More hairs present along main vein and margin.
- *Color.*—Young foliage upper side: Near RHS Yellow-Green 144A. Young foliage under side: Near RHS Green 138B. Mature foliage upper side: Near RHS Green 137A, but darker. Mature foliage under side: Near RHS Green 138B.
- *Venation.*—Type: Pinnate. Venation color upper side: Near RHS Yellow-Green N144A. Venation color under side: Near RHS Green 138B.
- *Petiole.*—Length: About 0.6 cm. Diameter: About 0.15 cm. Color: Upper Surface: Near RHS Yellow-Green N144D. Lower Surface: Near RHS Yellow-Green N144D.

FLOWER

Bloom period: Plants begin flowering in the Spring, and continue to produce flowers throughout Summer and Fall.

Flower:

*Arrangement.*—Axillary clusters of perfect, semi-double open funnel shaped individual flowers. Typically 3 to 7 flowers per cluster.

Inflorescence:

*Height.*—Average 14.0 cm.

*Diameter.*—Average 15.0 cm.

Peduncle:

*Length.*—Average 8.9 cm.

*Diameter.*—0.3 cm.

*Color.*—Near RHS Yellow-Green N144A.

*Texture.*—Densely pubescent.

*Aspect.*—Straight. Angle of attachment, approximately 35° angle from stem.

Flowers:

*Length.*—Average 4.1 cm.

*Diameter.*—Average 6.5 cm.

*Facing direction.*—Outwardly and upwardly facing.

*Persistent or self-cleaning.*—Petals self-cleaning.

*Fragrance.*—Very faint.

Tube:

*Tube length.*—Approximately 1.3 cm.

*Tube width a widest point.*—Approximately 1.2 cm.

*Tube width and narrowest point.*—Approximately 0.4 cm.

Petals:

*Unfused petal segments.*—Length: Approximately 2.5 cm. Width: Approximately 3.0 cm.

*Apex.*—Blunt, rounded with shallow, irregular lobes. Occasionally retuse.

*Shape of petal.*—Unfused portion, obovate.

*Petal margin.*—Entire. Aspect very slightly undulating.

*Petal arrangement.*—Overlapping, bilateral symmetry dissecting bottom petal. Petals fused approximately ⅓ fused from base.

*Petal number.*—5.

*Petal texture.*—Smooth.

*Color.*—Upper surface at first opening: Near RHS Red 53A. Under surface at first opening: Near RHS Red 53A. Inner surface at maturity: Near RHS Red 53B, 3 upper petals dotted with Greyed-Purple 1871A. Outer surface at maturity: Near RHS Red 53C. Upper surface at fading: Near RHS Red 53C, 3 upper petals dotted with Greyed-Purple 1871A. Under surface at fading: Near RHS Red 53C.

Bud:

*Shape.*—Elliptic.

*Length.*—3.1 cm.

*Diameter.*—1.3 cm.

*Color.*—Near RHS Red 53A.

Calyx/sepals:

*Quantity per flower.*—5 sepals.

*Shape.*—Narrow deltate.

*Length.*—0.7 cm.

*Width.*—0.3 cm.

*Apex.*—Acute.

*Base.*—Fused.

*Margin.*—Entire.

*Texture.*—Highly pubescent.

*Color.*—Inner Surface: Near RHS Yellow-Green 145A. Outer Surface: Near RHS Yellow-Green 145A.

REPRODUCTIVE ORGANS

Stamens:

*Number.*—5 full stams, 5 staminoidal structures, approximately 50% of the size of the full stamens.

*Length.*—2.6 cm.

*Width.*—0.1 cm.

*Color.*—Near RHS Red-Purple 58B.

*Anthers.*—Length: Approximately 0.3 cm. Color: Near RHS Red-Purple 59A. Pollen: Not observed.

Pistil:

*Number.*—1.

*Length.*—4.5 cm.

*Style.*—Length: Average 3.7 cm. Color: Near RHS Red 53D.

*Stigma.*—Globular, colored near Red 54A.

*Ovary.*—Sericeous texture. Approximately 0.3 cm in diameter. Colored near Yellow-Green 145A.

OTHER CHARACTERISTICS

Disease and pest resistance: Not observed to be susceptible nor resistant to normal diseases and pests of *Rhododendron.*

Temperature tolerance: USDA Zone 6.

Fruit/seed production: Not observed to date.

What is claimed is:

1. A new and distinct cultivar of *Rhododendron* plant named 'ROBLEZ' as herein illustrated and described.

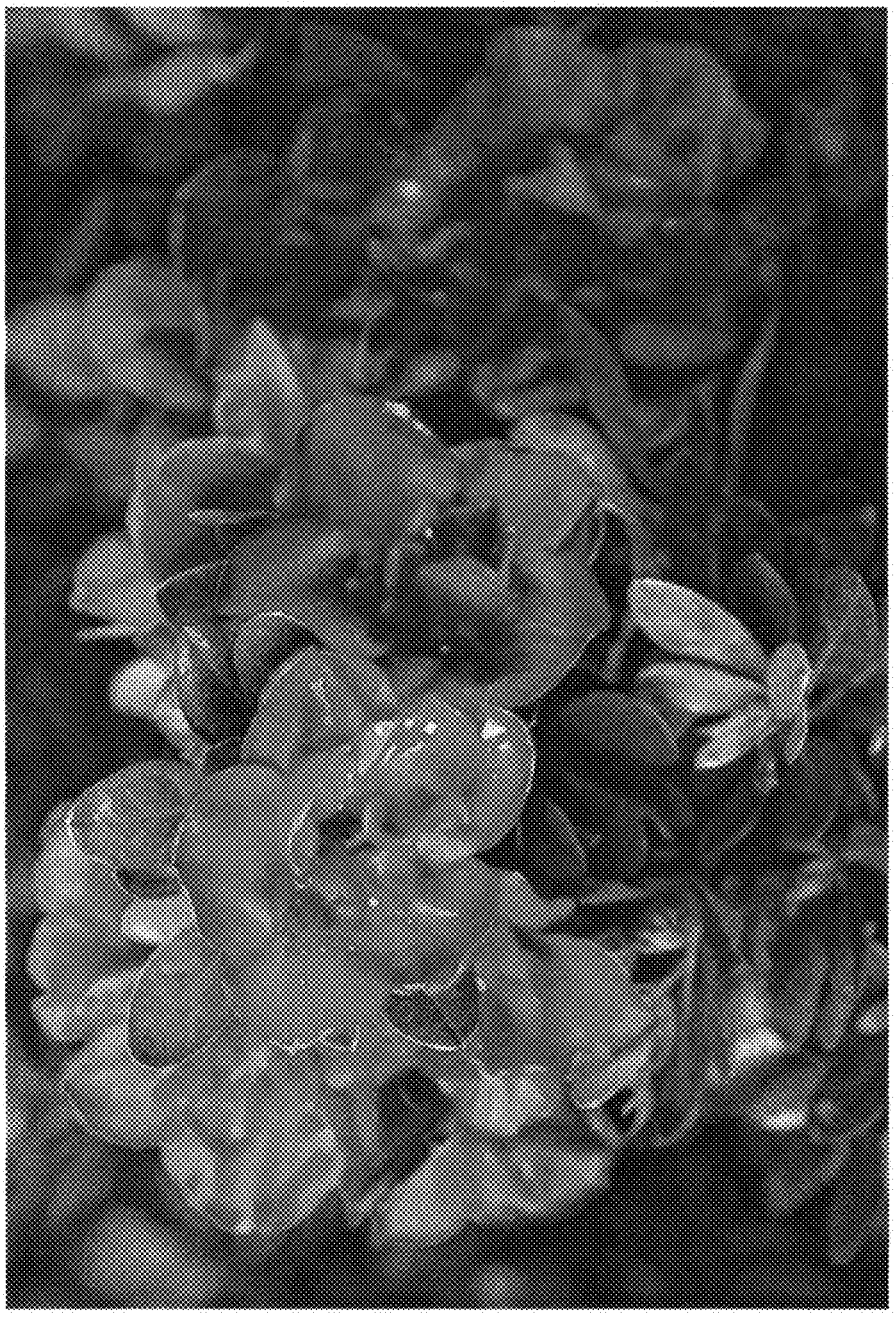

* * * * *